United States Patent
Treuner

[11] 3,994,893
[45] Nov. 30, 1976

[54] 4-AMINO DERIVATIVES OF PYROZOLO[1,5-a]QUINOXALINE-3-CARBOXYLIC ACID AND ESTERS

[75] Inventor: Uwe D. Treuner, Regensburg, Germany

[73] Assignee: E. R. Squibb & Sons, Inc., Princeton, N.J.

[22] Filed: Nov. 3, 1975

[21] Appl. No.: 628,277

[52] U.S. Cl. .................... 260/250 Q; 260/247.2 R; 260/247.2 B; 260/268 TR; 260/310 R; 424/248; 424/250
[51] Int. Cl.² ........................ C07D 487/04
[58] Field of Search ............... 260/250 Q, 250 QN

[56] References Cited
OTHER PUBLICATIONS

Burger et al., Medicinal Chem., 3rd Ed. pp. 1588–1589 (1971).
Eudokimo H. et al., Chem. Abs. 55, 5517c (1960).

*Primary Examiner*—Richard J. Gallagher
*Assistant Examiner*—Mark L. Berch
*Attorney, Agent, or Firm*—Lawrence S. Levinson; Merle J. Smith

[57] ABSTRACT

New 4-amino derivatives of pyrazolo[1,5-a]quinoxaline-3-carboxylic acid, esters and their salts have the formula

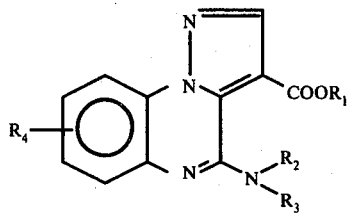

$R_1$ is hydrogen, lower alkyl or a salt forming ion;

$R_2$ and $R_3$ each is hydrogen, lower alkyl, cyclolower alkyl, phenyl, substituted phenyl, phenyl-lower alkylene, di-lower alkylamino-lower alkylene or $R_2$ and $R_3$ together with the nitrogen form an unsubstituted or substituted 5- or 6-membered nitrogen heterocyclic in which an additional nitrogen or oxygen may be present.

$R_4$ is hydrogen, lower alkyl or halogen.

The new compounds are useful as anti-inflammatory agents.

13 Claims, No Drawings

4-AMINO DERIVATIVES OF PYROZOLO[1,5-A]QUINOXALINE-3-CARBOXYLIC ACID AND ESTERS

SUMMARY OF THE INVENTION

This invention relates to new 4-amino derivatives of pyrazolo[1,5-a]quinoxaline-3-carboxylic acids and esters which have the formula

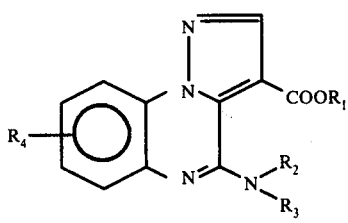

wherein $R_1$ is hydrogen or lower alkyl;

$R_2$ and $R_3$ each is hydrogen, lower alkyl, cyclo-lower alkyl, phenyl, substituted phenyl wherein the phenyl substituent is one or two simple substituents, i.e., halogen, lower alkyl, trifluoromethyl or carboxy, phenyl-lower alkylene, di-lower alkylamino-lower alkylene or the group

forms an unsubstituted or substituted 5- or 6-membered heterocyclic in which an additional nitrogen atom or oxygen atom may be present, i.e., pyrrolidino, piperidino, piperazinyl or morpholino, the substituent on the heterocyclic being a phenyl, a hydroxy-lower alkyl group or one or two lower alkyl groups;

$R_4$ is hydrogen, lower alkyl or halogen; and salts thereof.

The foregoing symbols have the same meaning throughout this specification.

DETAILED DESCRIPTION OF THE INVENTION

The various groups represented by the symbols are of the following kind:

The lower alkyl groups are straight or branched chain hydrocarbon groups having up to seven carbon atoms in the chain, e.g., methyl, ethyl, propyl, isopropyl, butyl, isobutyl, t-butyl, amyl, hexyl, heptyl, etc. The $C_1$–$C_4$ lower alkyl groups and especially $C_1$–$C_2$ groups are preferred.

The halogens are the four common halogens, but chlorine and bromine are preferred especially the first.

The basic amino group

is an acyclic amino group in which $R_2$ and $R_3$ each is hydrogen, lower alkyl, cyclo-lower alkyl, phenyl, substituted phenyl (wherein the phenyl substituent is one or two halogen, lower alkyl, carboxy or trifluoromethyl groups, preferably only one), phenyl-lower alkylene or di-lower alkylamino-lower alkylene (the lower alkyl and lower alkylene groups being similar to the lower alkyl groups described above, with the $C_1$–$C_4$ and $C_1$–$C_2$ groups constituting preferred and especially preferred members, respectively). The cyclo-lower alkyl groups are the three to seven carbon cycloaliphatics cyclopropyl, cyclobutyl, cyclopentyl, cyclohexyl and cycloheptyl, the three, six and seven membered rings being preferred, epecially the last two. Preferably only one of $R_2$ or $R_3$ is phenyl, substituted phenyl, phenyl-lower alkylene, cyclo-lower alkyl or di-lower alkylamino-lower alkylene, the other being hydrogen.

Such acyclic amino groups include, for example, amino, lower alkylamino (e.g., methylamino, ethylamino, propylamino, isopropylamino, etc.), di-lower alkylamino (e.g., dimethylamino, amino, diethylamino, dipropylamino, methylethylamino, etc.), anilino, (2-trifluoromethyl)anilino, 2-(chlorophenyl)amino, (4-bromophenyl)amino, (3,5-dichlorophenyl)amino, (3,4-dibromophenyl)amino, (2-carboxyphenyl)amino, (4-carboxyphenyl)amino, (4 -methylphenyl)amino, (3,5-dimethylphenyl)amino, benzylamino, phenethylamino, cyclopropylamino, cyclobutylamino, cyclopentylamino, cyclohexylamino, cycloheptylamino, dimethylaminomethylamino, dimethylaminoethylamino, (methylethyl)aminomethylamino, dipropylaminoethylamino, etc.

The basic amino group

also represents a heterocyclic radical wherein $R_2$ and $R_3$ join to complete one of the groups pyrrolidino, piperidino, morpholino or piperazinyl. The heterocyclic (preferably piperidino and piperazinyl) can also bear as a substituent a hydroxy-lower alkyl group, a phenyl group or one or two lower alkyl groups (preferably in the para-position, e.g., 4-methylpiperazinyl, 4-(hydroxyethyl) piperazinyl, 4-methylpiperidino, 4-phenyl-piperazinyl).

The products of the examples are prefered embodiments.

Especially preferred compounds of formula I are those wherein $R_1$ is lower alkyl, especially ethyl;

$R_2$ is hydrogen or lower alkyl, especially hydrogen;

$R_3$ is hydrogen, lower alkyl, (especially $C_1$–$C_4$-lower alkyl and particularly butyl), cyclo-lower alkyl (especially cyclopropyl, cyclohexyl and cycloheptyl), phenyl or the group

is morpholino, piperazinyl, lower alkyl-piperazinyl (especially 4-methylpiperazinyl), or 4-phenylpiperazinyl;

$R_4$ is hydrogen.

The compounds of formula I are produced from a 2-nitrophenylhydrazine of the formula

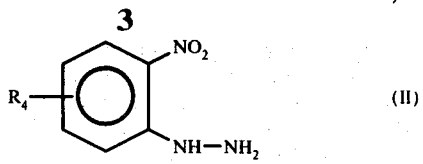

which is made to react with an alkoxymethyleneoxalic acid ester of the formula

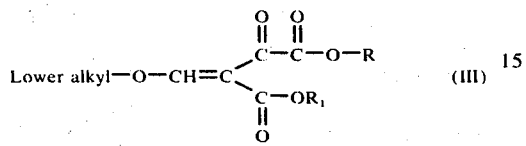

wherein R and $R_1$ each is lower alkyl, preferably ethyl, e.g., by heating at a temperature about reflux temperature in glacial acetic acid. The resulting compound of the formula

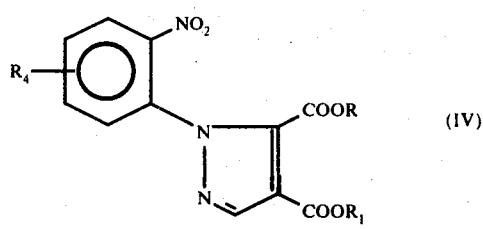

is hydrogenated in the presence of a catalyst like palladium on carbon in glacial acetic acid or an alcohol like ethanol or butanol, producing a compound of the formula

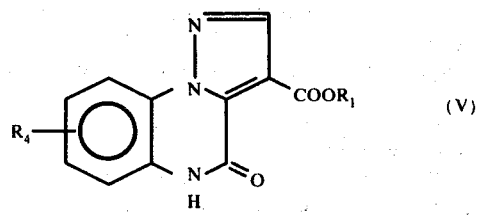

The intermediate of formula V is halogenated with a halogenating agent, e.g., a phosphorous oxyhalide like phosphorous oxychloride to produce a compound of the formula

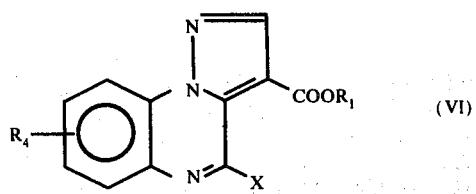

wherein X is halogen (preferably chlorine or bromine). The intermediate of formula VI can be treated by two alternative routes to obtain the products of formula I.

According to one alternative, the compound of formula VI is treated with an alkali metal alkoxide like sodium methoxide, potassium ethoxide or the like to obtain a compound of the formula

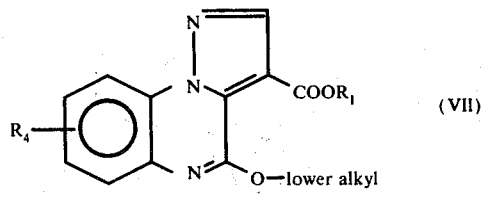

with a lower alkoxy group in the 4-position.

Compounds of formula I are now obtained by reacting the compound of formula VII with the appropriate amine of the formula

at elevated temperatures.

According to a second alternative the compound of formula VI is directly treated with the amine (VIII), e.g., in the presence of a base like triethylamine in a solvent like diethyleneglycoldimethyl ether, alcohol or the like.

The ester is converted to the acid ($R_1$=H) by hydrolysis, e.g., with an equivalent of base like sodium or potassium hydroxide in an alcohol like ethanol.

The new compounds of formula I form salts which are also part of this invention. The salts include acid addition salts, particularly the non-toxic, physiologically acceptable members. These salts are formed by reaction with one or more equivalents of any of a variety of inorganic and organic acids, especially the strong acids, providing acid addition salts including, for example, hydrohalides (especially hydrochloride and hydrobromide), sulfate, nitrate, borate, phosphate, oxalate, tartrate, maleate, citrate, acetate, ascorbate, succinate or aryl- or alkanesulfonates like benzenesulfonate, methanesulfonate, cyclohexanesulfamate and toluenesulfonate. The acid addition salts frequently provide a convenient means for isolating the product, e.g., by forming and precipitating a salt (which is not necessarily non-toxic) in an appropriate medium in which the salt is insoluble, then after separation of the salt, neutralizing with an equivalent of base such as barium hydroxide or sodium hydroxide, to obtain the free base of formula I. Other salts can then be formed from the free base by reaction with one or more equivalents of acid containing the desired anion.

Certain members, i.e., wherein R is hydrogen, form salts with metals, e.g., alkali metals like sodium, alkaline earth metals like calcium and magnesium, etc., e.g., by treating an ester, i.e., $R_1$ is lower alkyl, with an excess of base. These salts are useful to form soluble derivatives or as intermediates. They are also within the scope of the invention.

Additional experimental details are found in the examples.

The new compounds of this invention have antiinflammatory properties and are useful for administration orally or parenterally as antiinflammatory agents, for example, to reduce local inflammatory conditions such as those of an edematous nature or resulting from proliferation of connective tissue in various mammalian species such as rats, dogs and the like when given orally or parenterally in dosages of about 5 to 50 mg/kg/day, preferably 5 to 25 mg/kg/day, in single or 2 to 4 divided doses, as indicated by the carageenan edema assay in rats or delayed hypersensitivity skin reaction test.

The compounds of the invention can be utilized by formulating in compositions such as tablets, capsules or elixirs for oral administration or in sterile solutions or suspensions for parenteral administration. About 10 to 250 mg. of a compound or mixture of compounds of formula I or physiologically acceptable salt (preferably acid addition salt) is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup or elixir may contain the active compound, sucrose as a sweetening agent, methyl and propyl parabens as preservatives, a dye and a flavoring such as cherry or orange flavor. Of course, any material used in preparing the dosage unit should be pharmaceutically pure and substantially non-toxic in the amounts employed.

For topical administration as an antiinflammatory agent, a conventional lotion, ointment, or cream containing about 0.1 to 3 percent by weight of a compound of formula I or its salt is formulated.

The following examples are illustrative of the invention and constitute preferred embodiments. They also serve as models for the preparation of other members of the group which can be produced by suitale substitution of starting materials. All temperatures are in degrees celsius.

EXAMPLE 1 a) 1-(2-Nitrophenyl)-1H-pyrazole-4,5-dicarboxylic acid, diethyl ester 5 g. of 2-nitrophenylhydrazine are dissolved in 50 ml. of glacial acetic acid and 7.9 g. of ethoxymethyleneoxalic acid ethyl ester in 50 ml. of glacial acetic acid are slowly added dropwise. After the addition has been completed, the reaction mixture is refluxed for at least three hours. After cooling, the solvent is distilled off first under water vacuum and then under oil pump vacuum. The dark, oily residue is dissolved in 20 ml. of tetrahydrofuran, 10 ml. of ether are added and the mixture is kept in the refrigerator for 24 hours. The product, 1-(2-nitrophenyl)-1-H-pyrazole-4,5-dicarboxylic acid, diethyl ester, is obtained in the form of large crystals, yield 11.5 g. The product is recrystallized from cyclohexane and obtained as yellow crystals; yield 9.8 g., m.p. 45°–46°.

b) 4-Hydroxypyrazolo[1,5-a]quinoxaline-3-carboxylic acid, ethyl ester 50 g. of the product of part a are dissolved in 400 ml. of glacial acetic acid and hydrogenated at 65° in the presence of 0.2 g. of palladium on carbon. At the end of the hydrogen uptake, the solvent is distilled off and the residue is recrystallized from dioxane containing activated carbon to obtain 4-hydroxypyrazolo[1,5-a]quinoxaline-3-carboxylic acid, ethyl ester as white, matted needles; yield 28 g., m.p. 249°–251°.

c) 4-Chloropyrazolo[1,5-a]quinoxaline-3-carboxylic acid, ethyl ester 50 g. of the product of part b in 200 ml. of phosphorous oxychloride are refluxed for three hours. After distilling off the excess phosphorous oxychloride, 4-chloropyrazolo[1,5-a]quinoxaline-3-carboxylic acid, ethyl ester crystallizes. The distillation residue is stirred shortly with ice water and then the crude product is filtered off. The crude product is dried shortly over potassium hydroxide and recrystallized from acetone. The pure product is obtained as white needles; yield 39.5 g., m.p. 105°–106°.

d) 4-Butylamino)pyrazolo[1,5-a]quinoxaline-3-carboxylic acid, ethyl ester 7.98 g. of the product of part c together with 2.2 g of n-butylamine and 3 g. of triethylamine in 50 ml. of diethyleneglycol dimethyl ether are heated to boiling for one hour. After distilling off the solvent, water is added and the residue is recrystallized from ethanol. 4-(butylamino)pyrazolo[1,5-a]quinoxaline-3-carboxylic acid, ethyl ester is obtained as fine white crystals; yield 6.2 g., m.p. 96°.

EXAMPLE 2

4-Aminopyrazolo[1,5-a]quinoxaline-3-carboxylic acid, ethyl ester 2,76 g. of the chloro compound of Example 1 c is stirred for 10 hours with 25 ml. of saturated alcoholic ammonia solution at room temperature. The product, 4-aminopyrazolo[1,5-a]quinoxaline-3-carboxylic acid, ethyl ester, is obtained as a white precipitate which is filtered under suction, treated with water and recrystalized from ethanoldimethylformamide; yield 1.76 g., m.p. 235°–237°.

EXAMPLE 3

4-[(1-Methylpropyl)amino]pyrazolo[1,5-a]quinoxaline-3-carboxylic acid, ethyl ester By substituting an equivalent amount of (1-methylpropyl)amine for the n-butylamine in the procedure of Example 1 a, 4-[(1-methylpropyl)amino]pyrazolo[1,5- a]quinoxaline-3-carboxylic acid, ethyl ester is obtained, m.p. 82°–84°.

EXMAPLE 4

4-(Cyclopropylamino)pyrazolo[1.5-a]quinoxaline-3-carboxylic acid, ethyl ester By substituting an equivalent amount of cyclopropylamine for the n-butylamine in the procedure of Example 1 d, 4-(cyclopropylamino)pyrazolo[1,5-a]quinoxaline-3-carboxylic acid, ethyl ester is obtained, m.p. 167°–169°.

EXAMPLE 5

4-(Cyclohexylamino)pyrazolo[1,5-a]quinoxaline-3-carboxylic acid, ethyl ester By substituting an equivalent amount of cyclohexylamine for the n-butylamine in the procedure of Example 1 d, 4-(cyclohexylamino)pyrazolo[1,5-a]quinoxaline-3-carboxylic acid, ethyl ester is obtained, m.p. 132°–135°.

EXAMPLE 6

4-(Cycloheptylamino)pyrazolo[1,5-a]quinoxaline-3-carboxylic acid, ethyl ester By substituting an equivalent amount of cycloheptylamine for the n-butylamine in the procedure of Example 1 d, 4-(cycloheptylamino)pyrazolo[1,5-a]quinoxaline-3-carboxylic acid, ethyl ester is obtained, m.p. 114°–115°.

EXAMPLE 7

4-(4-Morpholinyl)pyrazolo[1,5-a]quinoxaline-3-carboxylic acid, ethyl ester

By substituting an equivalent amount of morpholine for the n-butylamine in the procedure of Example 1 d, 4-(4-morpholinyl)pyrazolo[1,5-a]quinoxaline-3-carboxylic acid, ethyl ester is obtained, m.p. 142°–143°.

EXAMPLE 8

4-(4-Methyl-1-piperazinyl)pyrazolo[1,5-a]quinoxaline-3-carboxylic acid, ethyl ester By substituting an equivalent amount of 4-methylpiperazine for the n-butylamine in the procedure of Example 1 d, 4-(4-methyl-1-piperazinyl)quinoxaline-3-carboxylic acid, ethyl ester is obtained, m.p. 234°–236°.

EXAMPLE 9

4-(4-Phenyl-1-piperazinyl)pyrazolo[1,5-a]quinoxaline-3-carboxylic acid, ethyl ester By substituting an equivalent amount of 4-phenylpiperazine for the n-butylamine in the procedure of Example 1 d, 4-(4-phenyl-1-piperazinyl)pyrazolo[1,5-a]quinoxaline-3-carboxylic acid, ethyl ester is obtained, m.p. 134°–135°.

EXAMPLE 10

4-(Phenylamino)pyrazolo[1,5-a]quinoxaline-3-carboxylic acid, ethyl ester

By substituting an equivalent of aniline for the n-butylamine in the procedure of Example 1 d, 4-(phenylamino)-pyrazolo[1,5-a]quinoxaline-3-carboxylic acid ethyl ester is obtained, m.p. 145°–147°.

EXAMPLE 11

4-(Phenylamino)pyrazolo[1,5-a]quinoxaline-3-carboxylic acid 2.5 g. of the product of Example 10 is stirred for 5 hours at 40° with an equivalent of alcoholic potassium hydroxide. After removal of the solvent, the residue is dissolved in water and acidified with acetic acid. The product, 4-(phenylamino)pyrazolo[1,5-a]quinoxaline-3-carboxylic acid is recrystallized from dimethylformamide, m.p. 283°–285°. Treatment of this product with ethanolic HCl gives the hydrochloride salt.

EXAMPLE 12

4-(Butylamino)pyrazolo[1,5-a]quinoxaline-3-carboxylic acid, ethyl ester a. 5.5 g. of 4-chloropyrazolo[1,5-a]quinoxaline-3-carboxylic acid, ethyl ester is heated for two hours with 10 ml. of a 2 molar sodium ethylate solution. The hot reaction solution is filtered and, upon cooling, 4-ethoxy-pyrazolo[1,5-a]quinoxaline-3-carboxylic acid, ethyl ester crystallizes in the form of white needles. The product is recrystallized from ethanol to obtain 3.4 g. of white crystals, m.p. 88°–90°.

b. 3 g. of the product of part a are heated in 10 ml. of n-butylamine for 30 minutes, whereupon the 4-ethoxy compound gradually goes into solution. 50 ml. of water are added. After stirring for a short time, the product, 4-(butylamino)-pyrazolo[1,5-a]quinoxaline-3-carboxylic acid, ethyl ester, is separated in solid form. Recrystallization from ethanol yields 2.3 g. of product, m.p. 95°–96°. Treatment of this product with alcoholic potassium hydroxide according to the procedure of Example 11 gives the free acid. Treatment of the ethyl ester with an excess of potassium hydroxide gives the potassium salt.

EXAMPLE 13

4-[3-(Dimethylamino)propylamino]pyrazolo[1,5-a]quinoxaline-3-carboxylic acid, ethyl ester 10 ml. of 3-[(dimethylamino)propyl]amine are poured over 5.5 g. of 4-chloropyrazolo[1,5-a]quinoxaline-3-carboxylic acid, ethyl ester. Upon warming, everything goes into solution. After stirring for one hour, 200 ml. of ether and 200 ml. of water are added and the mixture is stirred for an additional 30 minutes. The organic phase is washed with water and dried over sodium sulfate. Upon evaporating, 4-[3(dimethylamino)propylamino]pyrazolo[1,5-a]-quinoxaline-3-carboxylic acid, ethyl ester crystallizes and the product is recrystallized from ether-petroleum ether; yield 5.9 g., m.p. 72°–74°.

The following additional products are obtained by the procedure of Example 1 by substituting for the n-butylamine in part d the amine shown in the first column and, if desired, substituting an $R_4$-substituted nitrophenylhydrazine for the 2-nitrophenylhydrazine in part a. The free acids are obtained by hydrolysis as in Example 11.

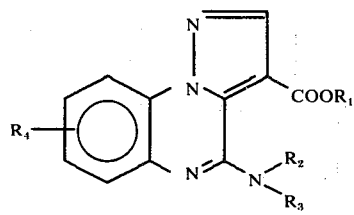

| Example | Amine | $R_1$ | $-N\begin{smallmatrix}R_2\\R_3\end{smallmatrix}$ | $R_4$ |
|---|---|---|---|---|
| 14 | $HN(C_2H_5)_2$ | $CH_3$ | $-N(C_2H_5)_2$ | H |
| 15 | $H_2N(C_2H_5)$ | H | $-NHC_2H_5$ | 7-Cl |
| 16 | $H_2NC_4H_9$ | $C_2H_5$ | $-NH$butyl | 8-$CH_3$ |
| 17 | $H_2N$–phenyl | $C_2H_5$ | $NH$–phenyl | 8-Br |
| 18 | $HN$⟨piperazine⟩$NH$ | $C_2H_5$ | $-N$⟨piperazine⟩$NH$ | H |
| 19 | $HN(CH_3)_2$ | $C_3H_7$ | $-N(CH_3)_2$ | 6-Br |
| 20 | $NH_3$ | $C_2H_5$ | $-NH_2$ | 8-$CH_3$ |
| 21 | $HN$⟨pyrrolidine⟩ | $C_2H_5$ | $-N$⟨pyrrolidine⟩ | H |
| 22 | $HN$⟨piperazine⟩$NCH_2CH_2OH$ | $CH_3$ | $-N$⟨piperazine⟩$N-CH_2CH_2OH$ | H |
| 23 | $HN$⟨piperidine⟩$-C_2H_5$ | $C_2H_5$ | $-N$⟨piperidine⟩$-C_2H_5$ | H |
| 24 | $HN$⟨3,5-dimethylpiperidine⟩ | $C_2H_5$ | $-N$⟨3,5-dimethylpiperidine⟩ | H |
| 25 | $H_2N$–phenyl | Na | $-NH$–phenyl | 9-Cl |
| 26 | $H_2N$–phenyl-$CF_3$ | $C_4H_9$ | $-NH$–phenyl-$CF_3$ | H |
| 27 | $H_2N$–phenyl-$Cl_2$ | H | $-NH$–phenyl-$Cl_2$ | H |
| 28 | $H_2N$–phenyl-Br | $C_2H_5$ | $-NH$–phenyl-Br | H |
| 29 | $H_2NCH_2N(CH_3)_2$ | H | $-NHCH_2N(CH_3)_2$ | 7-Cl |

-continued

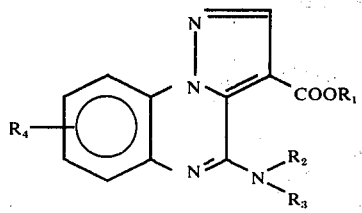

| Example | Amine | $R_1$ | $-N\langle{}^{R_2}_{R_3}$ | $R_4$ |
|---|---|---|---|---|
| 30 | $H_2N(CH_2)_2N(C_2H_5)_2$ | $CH_3$ | $-NHCH_2CH_2N(C_2H_5)_2$ | H |
| 31 | $HN(C_4H_9)_2$ | H | $N(C_4H_9)_2$ | H |
| 32 | $H_2N-\bigcirc-COOH$ | $C_2H_5$ | $-NH-\bigcirc-COOH$ | H |
| 33 | $H_2NCH_2-\bigcirc$ | $C_2H_5$ | $-NHCH_2-\bigcirc$ | H |
| 34 | $H_2N(CH_2)_2-\bigcirc$ | $C_2H_5$ | $-NHCH_2CH_2-\bigcirc$ | 8-$CH_3$ |
| 35 | $H_2NCH_3$ | Ca | $-NHCH_3$ | H |

What is claimed is:

1. A compound of the formula

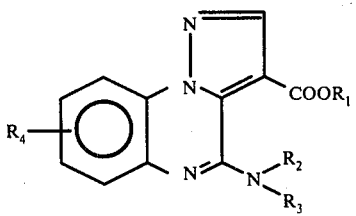

wherein $R_1$ is hydrogen or lower alkyl; $R_2$ and $R_3$ each is hydrogen, lower alkyl, cyclo-lower alkyl, phenyl, substituted phenyl wherein the phenyl substituent is one or two halogen, lower alkyl, carboxy or trifluoromethyl groups, phenyl-lower alkylene or di-lower alkylamino-lower alkylene or $R_2$ and $R_3$ complete one of the heterocyclics pyrrolidino or piperidino, said heterocyclics being unsubstituted or substituted with a phenyl group, hydroxy-lower alkyl group or one or two lower alkyl groups; $R_4$ is hydrogen, lower alkyl or halogen; and acid addition salts thereof.

2. A compound as in claim 1 wherein $R_1$, $R_2$ and $R_3$ each is hydrogen or lower alkyl; and $R_4$ is hydrogen.

3. A compound as in claim 1 wherein $R_1$ is lower alkyl; $R_2$ is hydrogen or lower alkyl; $R_3$ is hydrogen, lower alkyl, cyclo-lower alkyl or phenyl;

and $R_4$ is hydrogen.

4. A compound as in claim 1 wherein $R_4$ is hydrogen.

5. A compound as in claim 4 wherein

is amino.

6. A compound as in claim 4 wherein

is lower alkylamino.

7. A compound as in claim 4 wherein

is cyclo-lower alkylamino.

8. A compound as in claim 4 wherein

is anilino.
9. A compound as in claim 4 wherein $R_1$ is ethyl, $R_2$ is hydrogen, and $R_3$ is butyl.
10. A compound as in claim 8 wherein $R_1$ is ethyl.
11. A compound as in claim 4 wherein $R_1$ is ethyl and
is cyclohexylamino.
12. A compound as in claim 4 wherein $R_1$ is ethyl, $R_2$ is hydrogen and $R_3$ is 1-methylpropyl.
13. A compound as in claim 4 wherein $R_1$ is ethyl, $R_2$ is hydrogen and $R_3$ is n-butyl.
* * * * *

UNITED STATES PATENT AND TRADEMARK OFFICE
CERTIFICATE OF CORRECTION

PATENT NO. : 3,994,893
DATED : November 30, 1976
INVENTOR(S) : Uwe D. Treuner

It is certified that error appears in the above-identified patent and that said Letters Patent are hereby corrected as shown below:

Column 2, line 17, delete "amino".
Column 12, Claim 3, delete the formula " 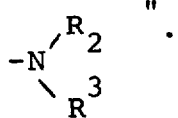 ".

Signed and Sealed this second Day of August 1977

[SEAL]

Attest:

RUTH C. MASON
*Attesting Officer*

C. MARSHALL DANN
*Commissioner of Patents and Trademarks*